(12) United States Patent
Lidgren et al.

(10) Patent No.: US 6,254,553 B1
(45) Date of Patent: *Jul. 3, 2001

(54) METHOD FOR ULTRASONIC TREATMENT OF DISC DISEASE

(75) Inventors: Lars Lidgren, Lund; Björn Strömqvist, Bjärred; Johan Severson, Lund, all of (SE)

(73) Assignee: Scandimed International AB, Sjobo (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/061,547

(22) Filed: Apr. 16, 1998

(30) Foreign Application Priority Data

Apr. 18, 1997 (SE) ................................................ 9701449

(51) Int. Cl.⁷ ................................................ A61N 7/02
(52) U.S. Cl. .......................... 601/3; 600/438; 600/439; 600/549
(58) Field of Search ........................... 601/2, 3; 600/639, 600/438, 549; 128/898; 607/96

(56) References Cited

U.S. PATENT DOCUMENTS

| | | |
|---|---|---|
| 4,787,394 | 11/1988 | Ogura . |
| 5,242,439 * | 9/1993 | Larsen et al. ........................ 606/15 |
| 5,291,890 * | 3/1994 | Cline et al. ........................... 601/3 |
| 5,327,884 | 7/1994 | Hardy et al. . |
| 5,433,739 * | 7/1995 | Sluitjer et al. ...................... 607/99 |
| 5,435,311 | 7/1995 | Umemura et al. . |
| 5,443,069 * | 8/1995 | Schaetzle ............................ 601/3 |
| 5,448,994 * | 9/1995 | Iinuma ................................ 601/3 |
| 5,501,655 | 3/1996 | Rolt et al. . |
| 5,571,147 * | 11/1996 | Sluijter et al. ..................... 607/96 |

FOREIGN PATENT DOCUMENTS

WO 93/17646   9/1993   (WO) .

* cited by examiner

Primary Examiner—Ruth S. Smith
(74) Attorney, Agent, or Firm—McCormick, Paulding & Huber LLP (57) ABSTRACT

The present invention relates to a device for non-invasive treatment of biological tissue, whereby the treatment aim at changing or degenerating said tissue. This device has a treatment transducer (2) comprising at least one ultrasonic transducer (3 and/or 4) which is provided to treat intervertebral discs (1), preferably nucleus pulposus (1a), by means of ultrasound, whereby the ultrasonic field of the ultrasonic transducer (3 and/or 4) is focused in said intervertebral disc (1), preferably in nucleus pulposus (1a), for heating the tissue therein, to such temperatures that the tissue in the focal area (5) degenerates, whereby the pressure in the intervertebral disc (1) and thus, the pressure against the spinal cord (6) is reduced.

20 Claims, 4 Drawing Sheets

METHOD FOR ULTRASONIC TREATMENT OF DISC DISEASE

THE BACKGROUND OF THE INVENTION

The present invention relates to a device and method for the non-invasive treatment of biological tissue, and in particular, the invention relates to a device and method for treating sciatica via ultrasonic heating focused on a focal area within an intervertebral disc, preferably on the nucleus pulposus, thus degenerating the tissue in the focal area, reducing pressure, and eliminating/reducing pain along the sciatic nerve.

The lifetime prevalence of sciatica is 40 percent, and 1–2 percent of the population will develop nerve compression by a lumbar disc herniation which requires invasive (surgical) treatment, usually during the fourth and fifth decades of life. Surgical removal of discal hernia, known as a discectomy, has been performed for almost seven decades. Diagnostic procedures ranging from myelography using oil, or nonionic contrast media, to computerized tomography (CT) and magnetic resonance imaging (MRI) has led to a rapid increase of the number of spinal operations with a diversity of surgical procedures.

There are four necessary prerequisites for intervention of disc herniation. First, the patient must experience functionally incapacitating pain in the leg extending below the knee with a nerve root distribution. Second, the nerve root must exhibit tension signs with or without neurological abnormalities. Third, the patient must experience failure of clinical improvement after four to eight weeks. Finally, the diagnoses must be confirmed (e.g. through imaging study).

The introduction of non-surgical or minimal invasive surgical procedures started in 1964 with chymopapain and chemonucleolysis which brought about the era of percutaneous treatment for herniated discs. The clinical success of chymopapain, which has good results in 60–75 percent of treatments, led to its extensive use. Unfortunately, it has an anaphylaxis rate estimated to be about 1 percent. The enzyme polymerizes the long chains of proteoglycans in the nucleus pulposus with subsequent loss of water binding capacity. This causes reduction in the volume and pressure of the nucleus pulposus, and results in a reduction in volume and pressure of the herniated fragment resulting in the immediate relief of sciatica in patients following chemanucleolysis. Most authors agree that relief of leg pain after chymopapain is less frequent than after surgery.

Several new methods using percutaneous techniques have evolved since 1975. Initially, these methods used endoscopic equipment. More recently, non-endoscopic techniques have been developed which use an automated percutaneous suction of tissue by means of a probe. Most recently, laser radiation (typically electromagnetic), created by external stimulation of a laser medium, has been used. Laser radiation treatment, however, requires a probe and is therefore invasive.

All these methods are to a certain extent invasive requiring surgical intervention. Disc infection and nerve root injury are potential complications of these methods. Although such complications are not as common as complications resulting from open surgery, they are an unnecessary risk.

The intervertebral disc is comparable to other non-vascularized biological tissue. It has a central nucleus pulposus with a gelatinous character and a surrounding stiffer anulus. The matrix in the disc includes several proteins with different rates of turn over and energy demand.

Currently, there is no non-invasive treatment available which will affect the disc in such a manner to reduce the volume and pressure in the nucleus pulposus thereby diminishing a discal hernia.

Attempts to achieve tissue degeneration with high intensity focused ultrasound (HIFU) have been going on for several years in cancer research projects. The advantage of ultrasound as a generator of energy, compared to, for example electromagnetic fields, is that ultrasound is a non-invasive method used to generate tissue heating at depths within the body. Focusing of the ultrasound, and placing the focus inside the tissue to be treated, makes the heating effect to develop at the desired location instead of at the skin and the tissue in between. Lele P., "Introduction of deep, local hyperthermia by ultrasound and electromagnetic fields. —Problems & Choices", Radiation and Environmental Biophysics 1980; 17: 205–217. If the transducer surface is spherical, the transducer has a fixed focus. Lele P., "Introduction of deep, local hyperthermia by ultrasound and electromagnetic fields. —Problems & Choices", Radiation and Environmental Biophysics 1980; 17: 205–217. It is also possible to achieve a flexible focus by means of phased array. Diederich C., Hynynen K., "The feasibility of using electrically focused ultrasound arrays to induce deep hyperthermia via body cavities", IEEE transactions on ultrasonics, ferroelectrics, and frequency control 1991; 38 (7): 634–643; Ebbini E., Cain C., "Asherical-Section Ultrasound Phased Array Applicator for Deep Localized Hyperthermia", IEEE Transactions on Biomedical Enfineering 1991; 38(7): 634–643; Ebbini E., Umemura S., Ibbini M., Cain C., "A cylindrical-section ultrasound phase-array applicator for hyperthermia cancer therapy", IEEE transactions on ultrasonics, ferroelectrics, and frequency control 1988; 35(5): 561–572; Holmer N., Lindström K., "Från A-mode till Phased array i Diagnostiskt ultraljud-Grunderna", editerad av Holmer, 65–67.

Prior art also includes numerous patent specifications relating to methods and devices in which ultrasound is utilized for various therapeutic purposes without any type of surgical operations on the patient. One such patent specification is U.S. Pat. No. 5,435,311 relating to an "ultrasound therapeutic system" for treatment of tissue, such as malignant tumors or various types of calculi like gallstone, kidney stone, etc. The device of U.S. Pat. No. 4,787,394 relating to an ultrasound therapy apparatus, has a similar purpose. Furthermore, other devices and methods utilizing ultrasound for a corresponding therapeutic purpose, are described in U.S. Pat. Nos. 5,327,884 and 5,501,655.

Similar tissue degeneration, as with ultrasound, can also be made with other methods, such as percutaneous laser discectomy and percutaneous radio-frequency coagulation by means of cauterizing instruments, however these methods are invasive. Buchelt M., Kutschera H., Katterschafka T., Kiss H., Schneider B., Ullrich R., "Erb.YAG and Hol.YAG Lasser Ablation of Meniscus and Intervertebral discs", Lasers in Surgery and Medicine 1992; 12: 375–381; Troussier B., Lebas J., Chirossel J., Peoc'h M., Grand S., Leviel J., Phelip X., "Percutaneous Intradiscal Radio-Frequency Thermocoagulation—A Cadaveric Study", Spine 1995; 20(15), 1713–1718.

SUMMARY OF THE INVENTION

The present invention is a device, and method of using the device, for treating sciatica via ultrasonic heating focused on a focal area within an intervertebral disc, preferably on the nucleus pulposus, thus degenerating the tissue in the focal area, reducing pressure therein, and eliminating/reducing pain along the sciatic nerve.

The object of the present invention is to provide a device for the noninvasive treatment of sciatia; particularly, the treatment of a herniated intervertebral disc by reduction of the volume of the nucleus pulposus. The present invention uses ultrasound to treat sciatia by focusing on a focal area within the intevertebral discs, preferably the nucleus pulposus. The reduction of the volume of the nucleus pulposus is achieved by a device having a treatment transducer with at least one ultrasonic transducer, which transmits ultrasonic waves having a frequency of 0.5 to 2.5 megahertz. The ultrasonic field of the ultrasonic transducer is focused on the intervertebral disc, preferably in the nucleus pulposus. The ultrasonic transducers of the treatment transducer transmits an ultrasonic field which heats the tissue, in a focal area of the intervertebral disc, to temperatures in the range of 45 to 80° C. so that the tissue in the focal area degenerates thus reducing the pressure in the intervertebral disc. The duration of the heating in the focal area is for a time period of 5 to 60 minutes per treatment. The reduction of pressure in the intervertebral disc reduces the pressure against the spinal cord.

By providing the device with said characterizing features, it is possible to treat intervertebral discs, preferably nucleus pulposus, in a lenient manner without degenerating tissue outside the intervertebral disc and this treatment can be carried through in a noninvasive manner. One does not have to insert foreign objects into the body and obviates thereby the risks and additional costs this might incur.

These and other objects of the present invention will become readily apparent upon further review of the following specification and drawings.

DETAILED DESCRIPTION OF THE PREFERRED EMBODIMENTS

Figure 1:
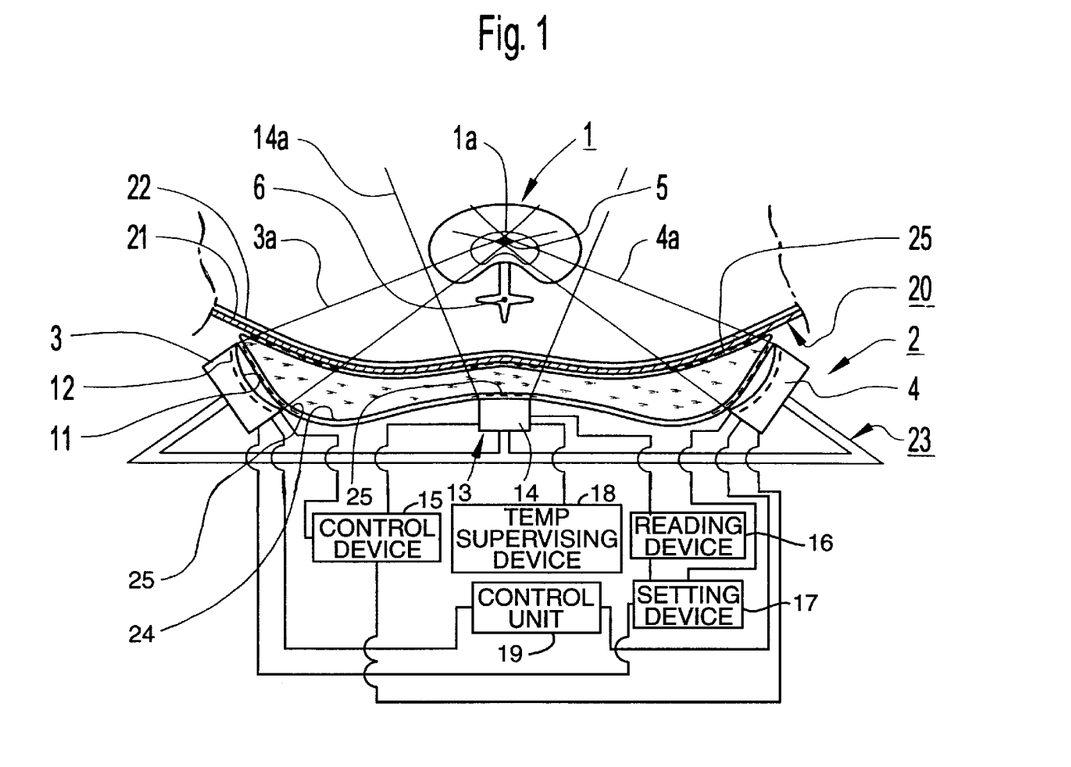
FIG. 1 is a schematic illustration of a device according to the present invention depicting treatment of an intervertebral disc, whereby a treatment table is shown in cross-section.
Figure 5:
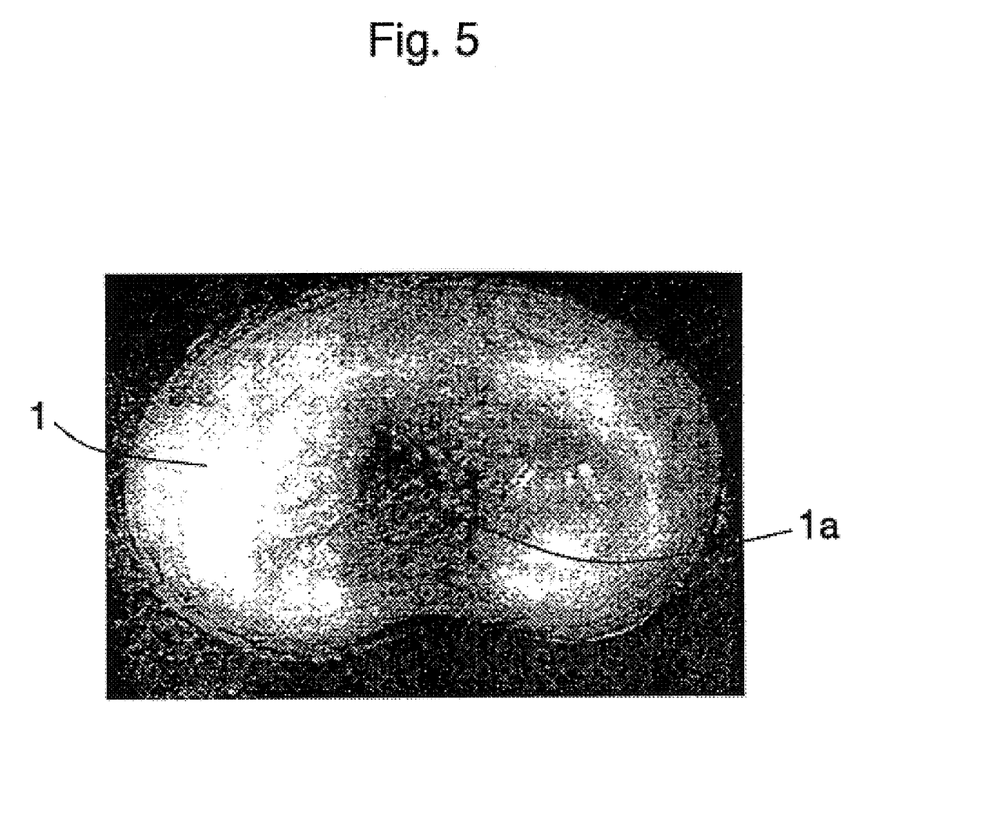
FIG. 5 is a picture of an intervertebral disc treated with the device according to the present invention.

The device illustrated in the drawings is intended for treatment of biological issues in the form of intervertebral discs 1, preferably nucleus pulposus 1a. For this urpose, the device comprises a treatment transducer 2 which includes two herapeutic ultrasonic transducers 3 and 4, as shown schematically in FIG. 1. These are arranged to each transmit an ultrasonic field 3a and 4a respectively, such that these meet to define a focal area 5. During treatment, the focal area 5 is located in the intervertebral disc 1, preferably nucleus pulposus 1a, which is to be treated by heating the tissue therein to such temperature that the tissue in the focal area 5 degenerates, whereby the pressure in the intervertebral disc 1 and thus, the pressure against the spinal cord 6, is reduced. FIG. 5 shows the intervertebral disc 1 and the nucleus pulposus 1a which are the treatment areas of the present invention.

The therapeutic ultrasonic transducers 3 and 4 are provided to transmit ultrasonic fields 3a and 4a which do not heat biological tissue outside the focal area such that it degenerates. By using at least two therapeutic ultrasonic transducers 3 and 4, the ultrasound effect is distributed over larger areas and therefore, a lower power per transducer can be used. This arrangement results in minimal eventual heat increases in the skin relative to the power put in the intervertebral disc 1 by the two therapeutic ultrasonic transducers 3 and 4. In other words, neither therapeutic ultrasonic transducer 3 or 4 produces large enough of an ultrasound effect alone to heat the tissue to the point of degeneration. The combined ultrasound effect of both of the therapeutic ultrasonic transducers 3 and 4 together is enough to heat the tissue where the two ultrasonic fields 3a and 4a combine (i.e., coincide) to degenerate the tissue in the focal area 5.

The power and frequency of the ultrasonic fields 3a and 4a, the temperature of the tissue in the focal area 5 and the transmitting time of the ultrasonic fields 3a and 4a may vary depending on various factors, but the frequency should lie within the range of 0.5–2.5 MHz. The temperature of the tissue in the focal area should be within the range of 45–80° C. This range of temperatures is the range at which tissue degeneration occurs. Temperatures below this range will not result in tissue degeneration. The total transmitting time of the ultrasonic fields 3a and 4a should be within the interval of 5–60 minutes.

The therapeutic ultrasonic transducers 3 and 4 can be arranged to transmit ultrasonic fields 3a and 4a, the focal area 5 of which is adaptable relative to the space M between the end plates 7 and 8 surrounded by the vertebrae 9 and 10 and which surround the intervertebral disc 1, such that the focal area 5 lies between the end plates 7 and 8 without heating thereof to tissue-degenerating temperatures, i.e., without heating the surrounding tissue above 44° C.

Figure 3:
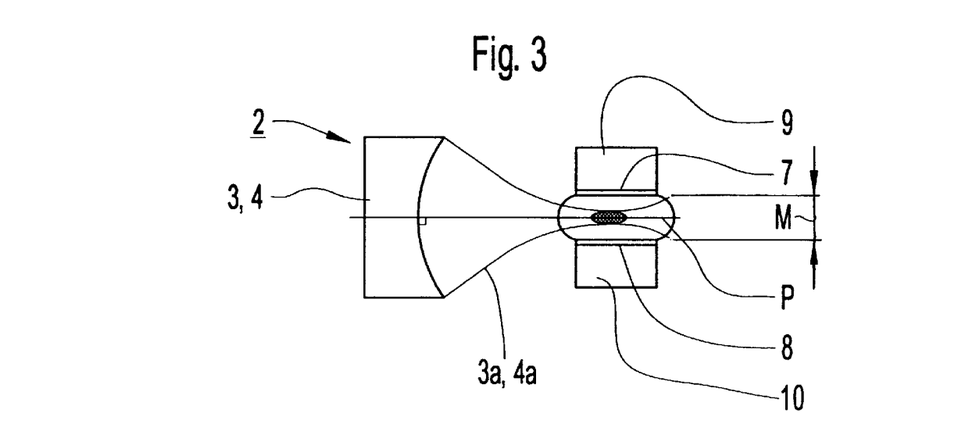
FIG. 3 schematically illustrates a treatment transducer forming part of the device of FIG. 1, and its ultrasonic field during the treatment of an intervertebral disc.

A focal area 5 with such adapted extension can be obtained by providing the therapeutic ultrasonic transducers 3 and 4 respectively, with means 11, preferably in the form of transducer elements with concave spherical transducer surfaces, for focusing each ultrasonic fields 3a or 4a. In this manner, a larger or better focus is achieved, and the focal area 5 has a substantially planar extension, as is shown in FIG. 3.

The therapeutic ultrasonic transducers 3 and 4 may also include means 12 for, if required, displacing the focal area 5, adapted preferably as mentioned to the space M between the end plates 7 and 8, to the intervertebral disc 1, preferably nucleus pulposus 1a. These means 12 can be transducer elements of the phased array type.

For being able to locate the focal area 5 in the intervertebral disc 1, preferably nucleus pulposus 1a, it may sometimes, depending on the relative positions of the therapeutic ultrasonic transducers 3 and 4 and the intervertebral disc 1, be advantageous or necessary to shrink or reduce the extension of one or both the ultrasonic fields 3a and/or 4a for avoiding heating of tissue outside the intervertebral disc 1 which should not be heated to tissue-degenerating temperatures. This can be achieved while each therapeutic ultrasonic transducer 3 or 4 has a plurality of means 12, preferably the transducers of phased array type, to momentarily deactivate, or put out of operation, each therapeutic ultrasonic transducer in order to reduce the extension of the ultrasonic field 3a and/or 4a.

The therapeutic ultrasonic transducers 3 and 4 can preferably be located relative to the intervertebral disc 1 so that they transmit ultrasonic fields 3a and 4awhich together define a focal area 5 with a substantially planar extension, and which are situated substantially parallel with and in a plane P wherein the intervertebral disc 1 is located.

The therapeutic ultrasonic transducers 3 and 4 can be arranged to transmit ultrasonic fields 3a and 4a with a focal area 5 the extension of which can be varied for adaptation to the size of the intervertebral disc 1 and/or nucleus pulposus 1a.

A diagnostic device 13 which includes at least one diagnostic ultrasonic transducer 14 which is provided, prior to the ultrasound treatment, to transmit an ultrasonic field 14a for registering the location of the intervertebral disc 1. The position of the therapeutic ultrasonic transducers 3 and 4 relative to the diagnostic ultrasonic transducer 14 are also known and in this way, their positions relative to the intervertebral disc 1 can be determined. The therapeutic ultrasonic transducers 3 and 4 are controlled depending on information registered in the diagnostic device 13 regarding the current position of the intervertebral disc 1, preferably nucleus pulposus 1a, so that the focal area 5 is moved to coincide with the intervertebral disc 1, preferably nucleus pulposus 1a. The orientation of the therapeutic ultrasonic transducers 3 and 4 can be controlled by changing their positions relative to their attachments. The control of their positions can be facilitated by a computer.

The control of the therapeutic ultrasonic transducers 3 and 4 can be carried through by means of a control device 15 either automatically or by a surgeon marking on a screen (not shown) a point/an area in nucleus pulposus 1a in which the focal area 5 is desired. A computer (not shown) can determine the necessary parameters in the therapeutic ultrasonic transducers 3 and 4 such that the focal area 5 becomes correct.

In the preferred embodiment, a reading device 16 is provided for registering displacements of the intervertebral disc 1 relative to the therapeutic ultrasonic transducers 3 and 4 which occur when the patient moves during treatment. Also preferably, a setting device 17 is provided to automatically control the therapeutic ultrasonic transducers 3 and 4 to set so that the focal area 5 will lie in the intervertebral disc 1, preferably nucleus pulposus 1a, after the displacement.

Also a non-invasive temperature-supervising device 18 for supervising the temperature in the intervertebral disc 1 during treatment is provided in the preferred embodiment. This temperature-supervising device 18, preferably, cooperates with a control unit 19 which is provided to control the therapeutic ultrasonic transducers 3 and 4 such that undesired temperature changes in the intervertebral disc 1 are prevented during treatment.

The temperature-supervising device 18, preferably, cooperates with the diagnostic ultrasonic transducer 14 of the diagnostic device 13 for supervising or monitoring the temperature in the intervertebral disc 1 by means ultrasound.

The therapeutic ultrasonic transducers 3 and 4 are preferably arranged obliquely behind the spine on opposite sides of the spinal cord 6, so that they can transmit their ultrasonic fields 3a and 4a in a direction beside the spinal cord 6 and on opposite sides thereof so that they meet in front thereof in order to together define the focal area 5 in the intervertebral disc 1, preferably nucleus pulposus 1a.

During treatment, a tretment table 20 can be used, which has a support surface 21 for the patient 22. This support surface 21 can be curved or settable into a curved shape such that the space M between the vertebrae 9 and 10 at the intervertebral disc 1 to be treated, increases when the patient 22 rests with his or her back against the support surface 21.

The therapeutic ultrasonic transducers 3 and 4 and the diagnostic ultrasonic transducer 14 are preferably mounted on a frame 23, whereby the mutual positions of the transducers 3, 4 and 14 can be known. The frame 23 with the transducers 3, 4 and 14 is preferably displaceable relative to the treatment table 20 and the patient 22 for setting the transducers 3, 4 and 14 relative to an intervertebral disc 1, preferably nucleus pulposus 1a, to be treated, in a patient 22 on the treatment table 20.

To avoid disturbances of the ultrasonic fields 3a and 4a transmitted by said transducers 3, 4 and 14, a gasvoid liquid in a liquid container 24 is preferably located between the transducers and the adjacent skin of the patient 22.

Figure 2:
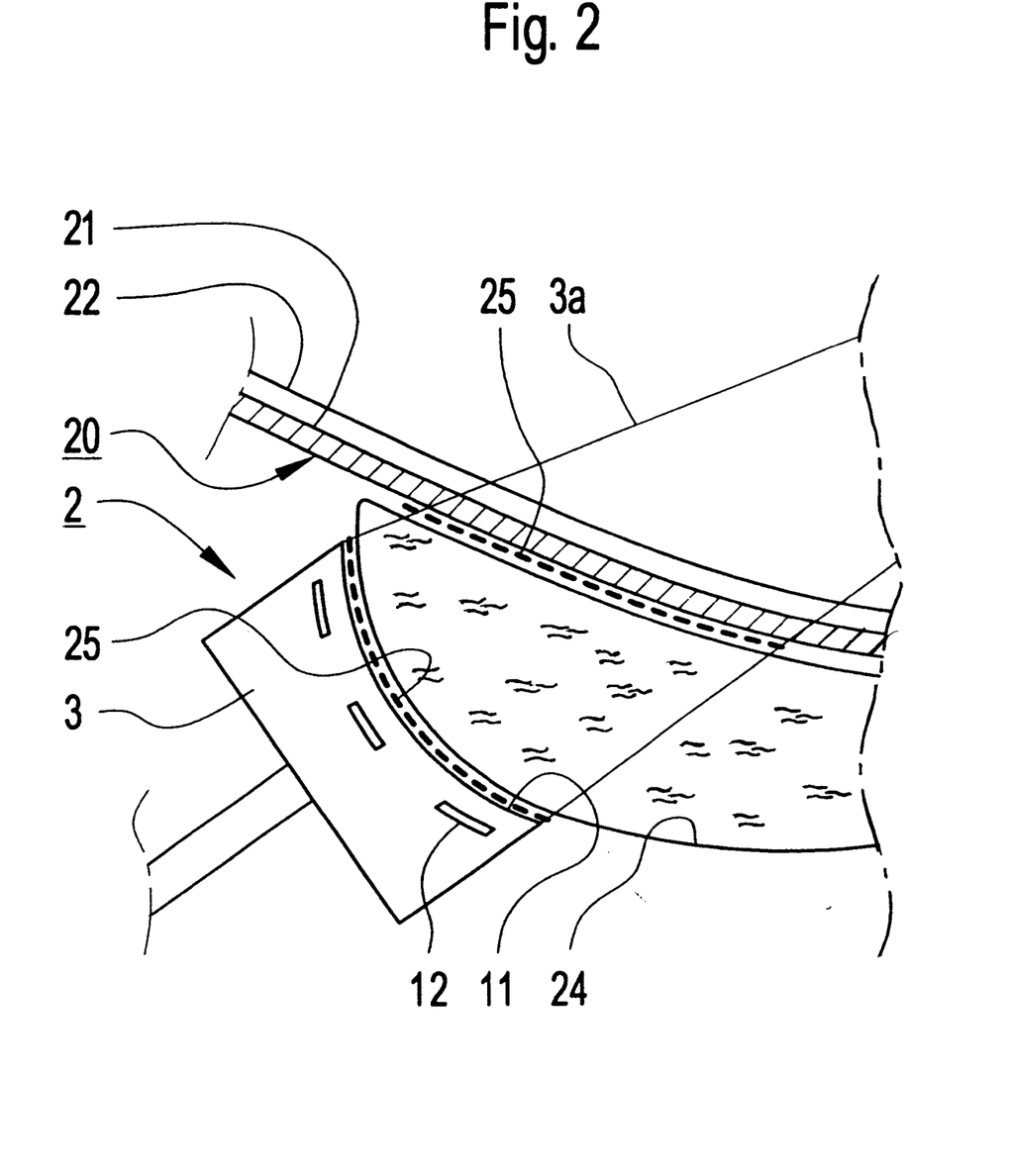
FIG. 2 illustrates an enlarged part of the device of FIG. 1.

Air between the transducers 3, 4 and 14, the liquid container 24 and adjacent skin is preferably removed by locating a gel 25 as schematically illustrated with broken lines, as seen schematically in FIG. 2. The gel 25 serves to further avoid disturbances of the ultrasonic fields 3a and 4a.

Treatment by means of the device described above is shown in the flow chart of FIG. 4. It has been determined which intervertebral disc 1 should be treated prior to the treatment described in the flow chart.

By means of an "ultrasound picture" obtained from the diagnostic device 13, the frame 23 and the patient 22 and eventually the therapeutic ultrasonic transducers 3 and 4 are oriented separately so that the angle of incidence of the therapeutic transducers 3 and 4 is correct. With the aid of the "ultrasound picture", proper positioning is achieved so that the ultrasonic fields 3a and 4a of the therapeutic ultrasonic transducers 3 and 4 lie in the same plane P as the intervertebral disc 1 to be treated, and so that the therapeutic therapeutic transducers 3 and 4 are directed towards the patient 22 from behind. On the above-mentioned screen, a point in the nucleus pulposus 1a is marked in which the focal area 5 (a so called movable focus which is displaced by means of the abovementioned means 12) for the therapeutic ultrasonic transducers 3 and 4 shall be located. A computer then establish the requirements for the various transducer elements in the therapeutic ultrasonic transducers 3 and 4. Eventually, adjacent bones can be marked as zones which the ultrasonic fields 3a and 4a are not allowed to reach.

The computer may, for example, deactivate the transducer elements which are closest and reduces thereby the size of the ultrasonic field 3a or 4a in question. This reduction of the ultrasonic field 3a and/or 4a can be compensated with a longer treatment time and/or treatment effect. The "fixed focus N" mentioned in the flow chart, depicted in FIG. 4, is the focal area obtained by means of the above-mentioned means 11.

Figure 4:
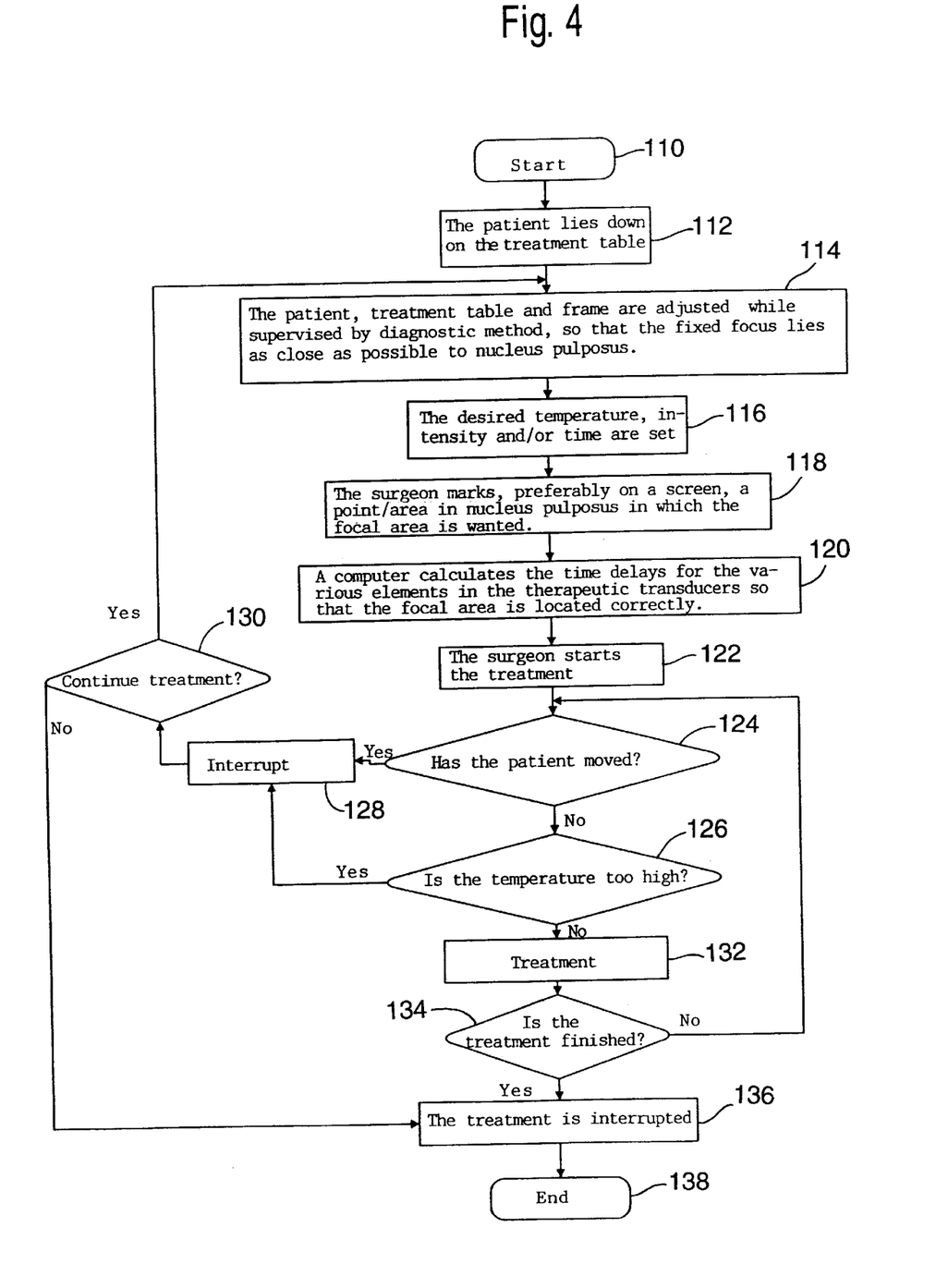
FIG. 4 is a flow chart describing the method of treatment of an intervertebral disc according to the present invention.

The flow chart, FIG. 4, depicts the necessary steps of the method of the present invention and also shows the steps which a computer may control. The treatment is initialized at start field 110. In the preliminary field 112, patient lies down on the treatment table. Then the adjustment field 114 where the patient and device of the current invention are so arranged as to place the fixed focus as close to the nucleus pulposus 1a as possible. The next field, of the flow chart, is the setting field 116 and depicts the initial parameters, temperature, intensity and or time, that the computer which controls the device of the present invention is set. The term setting is used herein to be the input to determine the parameters indicated. The next field is the marking field 118 wherein the surgeon marks where the focal area is desired. The time delay field 120 follows wherein the computer determines the time delays for the various elements in the therapeutic transducers to assure correct location of the focal area. The input focal area is defined to be the focal area as input by the surgeon in the marking field 118. The actual focal area is defined to the focal area as defined by the intersection of the ultrasonic fields generated from at least two directions.

Surgeon start field 122 depicts the relative sequence when the surgeon initiates the treatment. The computer monitoring the device checks to see if the patient has moved in the movement field 124. If the patient has moved and the decision is yes, then the interrupt field 128 is initiated. When the interrupt field 128 is initiated the computer checks to find the decision of whether the treatment should continue. If treatment should be continued with a yes decision, the flow chart returns to just prior to the adjustment field 114 and the patient and equipment are readjusted. If the patient has not moved the computer checks whether the temperature is too high as depicted in the temperature field 126. If the answer is yes, the temperature is too high, than the interrupt field 128 is initiated. If the answer is no the temperature is not to high, than the treatment is continued, depicted as treatment field 132.

The computer checks to see if treatment is finished at field 134, if not the computer loops back to just before the movement field 124, checks to see if the patient has moved, the temperature and so forth. The treatment continues until interrupted at field 128 with a no on the continue treatment or until the treatment is interrupted at field 136 at which time the treatment comes to an end at field 138. The term looping is used herein to refer to when the computer loops back to just before the movement field 124.

It should also be mentioned that instead of ultrasonic transducers, other therapeutic and/or diagnostic transducers, transmitters or applicators, e.g. transducers or transmitters of electromagnetic radiation, can be used in the device described above.

Drugs can be used in connection with and/or after treatment with the above-mentioned device, namely pressure reducing/volume decreasing drugs, such as steroids or corticosteroides (with or without antibacterials) available, for example, as CORTISON™, and/or dehydrating drugs, such as furosemide available, for example, as IMPUGAN™, and/or anti-inflammatory drugs, such as diclofenac sodium available, for example, as VOLTAREN™.

By means of the pressure reducing/volume decreasing drugs, it is possible, in connection with and/or after treatment with ultrasound, to improve the pressure reduction/volume decrease in nucleus pulposus obtained thereby.

By means of the dehydrating drugs, it is possible to improve the removal of fluid from the treatment area in connection with and/or after treatment with ultrasound.

By means of said anti-inflammatory drugs, it is possible to oppose inflammations in the treatment area in connection with and/or after treatment with ultrasound.

The invention is not limited to the device described above and illustrated in the drawings, but may vary within the scope of the following claims. Thus, the device may include more than one treatment transducer 2, there may be one, two or another suitable number of therapeutic ultrasonic transducers and the diagnostic device 13 can operate with something else other than ultrasound.

Instead of the patient 22 lying on his back on a treatment table 20, whereby the treatment equipment is situated beneath his or her back, the patient 22 and treatment equipment can be positioned otherwise. Thus, the patient 22 can for example be lying on his or her face and the treatment equipment be mounted on an arm permitting location thereof in a treatment position.

REFERENCES

Billard BE, Hynynen K and Roemer R B, 1990, Effects of physical parameters on high temperature ultrasound hyperhtemia. Ultrasound in Med. & Biol., 16 (4), 409–420

Buchelt M, Kutschera H-P, Katterschafka T, Kiss H, Schneider B and Ullrich R, 1992, Erb.YAG and Hol.YAG Laser Ablation of Meniscus and Intervertebral discs. Lasers in Surgery and Medicine, 12, 375–381

Bush N L, Rivens I, ter Haar G R and Bamber J C, 1993, Acoustic properties of lesions generated with an ultrasound therapy system. Ultrasound in Med & Biol, 19 (9), 789–801

Diederich C J and Hynynen K, 1991, The feasibility of using electrically focused ultrasound arrays to induce deep hyperthermia via body cavities. IEEE transactions on ultrasonics, ferroelectrics, and frequency control, 38 (3), 207–219

Ebbini E S and Cain C A, 1991, A Spherical-Section Ultrasound Phased Array Applicator for Deep Localized Hyperthermia. IEEE Transactions on Biomedical Engineering, 38 (7), 634–643

Ebbini E S, Umemura S-I, Ibbini M and Cain C A, 1988, A cylindrical-section ultrasound phased-array applicator for hyperthemia cancer therapy. IEEE transactions on ultrasonics, ferroelectrics, and frequency control, 35 (5), 561–572

Holmer N-G and Lindström K, 198?, Från A-mode till Phased array i Diagnostiskt ultraljud-Grunderna, editerad av Holmer, s 65–67

Lele P P, 1980, Induction of deep, local hyperthermia by ultrasound and electromagnetic fields. —Problems & choices. Radiation and Environmental Biophysics, 17, 205–217

Linke C A, Carstensen E L, Frizzell L A, Elbadawi A and Fridd C W, 1973, Localized tissue destruction by high-intensity focused ultrasound. Arch Surg, 107 (6), 887–891

Sibille A, Prat F, Chapelon J-Y, El Fadil F A, Henry L, Theillère Y, Ponchon T and Cathignol D, 1993, Extracorporeal ablation of liver tissues by high intensity focused ultrasound. Oncology, 50, 375–379

Troussier B, Lebas J F, Chirossel J P, Peoc'h M, Grand S, Leviel J L and Phelip X, 1995, Percutaneous Intradiscal Radio-Frequency Thermocoagulation—A Cadaveric Study. Spine, 20 (15), 1713–1718

What is claimed is:

1. A method for the non-invasive treatment of sciatica comprising the steps of:

creating ultrasonic fields from at least two laterally spaced therapeutic ultrasonic transducers of the phased array type, which therapeuthic ultrasonic transducers can be controlled in response to an external signal so as to generate a varying intensity of their ultrasonic fields, focusing these ultrasonic fields in a focal area defined between the plates of the intervertebral disc by providing the focal area between these plates from the therapeutic ultrasonic transducers, arranging the therapeutic ultrasonic transducers obliquely with respect to a plane containing the patient's spinal cord and the centerline of the patient's intervertebral discs, heating the tissue in the focal area of the ultrasonic fields to a temperature in the range of 45° C. to 80° C., controlling the ultrasonic fields from at least two laterally spaced therapeutic ultrasonic transducers in both strength and time so as to avoid heating the spinal cord and other surrounding biological tissue outside the focal area between the disc plates to tissue-degenerating temperatures, and monitoring the patient's physical location relative to the transducers, and moving the focal area in response to patient movement, so that the ultrasonic fields from the two laterally spaced obliquely directed therapeutic ultrasonic transducers are accurately focused in the area between the patient's intervertebral disc plates.

2. The method according to claim 1 wherein the ultrasonic field created has a frequency in the range of 0.5 to 2.5 megahertz.

3. The method according to claim 1 wherein the time period for so treating the intervertebral disc area between the plates from the ultrasonic fields is in the range of 5 to 60 minutes.

4. The method according to claim 1 wherein the step of focusing the ultrasonic fields in a focal area are facilitated by transducer elements each having a concave spherical transducer surface.

5. The method according to claim 1 further comprising the steps of sensing the temperature of a point in the patient outside the focal area between the obliquely directed focused ultrasonic fields, and in close proximity to the area of the patient's spinal cord, and providing the controlling signal to the phased array transducers by activating and deactivating selected transducers in order to achieve a target strength of the ultrasonic field as well as a target time period.

6. The method according to claim 1 wherein the focusing of the ultrasonic fields lies at a relatively narrow region between the plates of the intervertebral discs as compared to the width of the obliquely directed focused ultrasonic fields.

7. The method according to claim 1 further comprising the step of providing a resilient liquid-filled compliant container adjacent to the skin of the patient, and directing the focused ultrasonic fields from the transducers through such liquid, then through the patient's skin, into the focal area between the intervertebral disc plates of the patient.

8. The method according to claim 1 further comprising the steps of:

supervising the temperature in the intervertebral disc by ultrasound during treatment, and controlling the ultrasonic transducers of the treatment transducer such that undesired temperature changes in the intervertebral disc are prevented.

9. The method according to claim 1 wherein the step of heating the tissue in the focal area of the ultrasonic fields is to a temperature in the range of 45° C. to 50° C., and the focal area is the nucleus pulposus.

10. The method according to claim 1 further comprising:

the step of administering bio-effecting drugs taken from the group consisting of anti-inflamatory drug, dehydrating drug, pressure reducing/volume decreasing drugs, and combinations thereof.

11. The method according to claim 10 wherein the bio-effecting drugs are taken from the group consisting of furosemide, diclofenac sodium, steroids, corticosteroids, and combinations thereof.

12. The method according to claim 1 further comprising:

the step of providing a computerized system to automate treatment and to monitor time, intensity, temperature and location of the focal area wherein the system executes commands comprising the steps of setting parameters to establish temperature in the focal area, the time for treatment, and the intensity;

inputting the location of the focal area to be heated;

calculating time delays for various elements in the therapeutic transducers so that the focal area is located correctly;

starting and maintaining treatment by transmitting ultrasonic fields from at least two directions to meet at the focal area, the ultrasonic fields having the set intensity and heating the focal area to the set temperature;

looping to check for impermissible movement of the input focal area relative to an actual focal area, and impermissible temperature range in the actual focal area;

selecting to reset treatment or terminate treatment if impermissible movement and/or temperature are detected; and terminating treatment upon completion thereof when the set time expires.

13. The method of claim 1, further comprising the step of controlling the ultrasonic fields so as to avoid undesired temperature changes during treatment.

14. A method for the non-invasive treatment of disc disease comprising the steps of:

creating ultrasonic fields from at least two laterally spaced therapeutic ultrasonic transducers of the phased array type, which therapeutic ultrasonic transducers can be controlled in response to an external signal so as to generate a varying intensity of their ultrasonic fields;

focusing these ultrasonic fields in a focal area defined between the plates of the intervertebral disc by providing the focal area between these plates from the therapeutic ultrasonic transducers, arranging the therapeutic ultrasonic transducers obliquely with respect to a plane containing the patient's spinal cord and the centerline of the patient's intervertebral discs, wherein the focusing of the ultrasonic fields lies at a relatively narrow region between the plates of the intervertebral discs as compared to the width of the obliquely directed focused ultrasonic fields;

heating the tissue in the focal area of the ultrasonic fields to a temperature in the range of 45° C. to 65° C.;

controlling the ultrasonic fields from at least two laterally spaced therapeutic ultrasonic transducers in both strength and time so as to avoid heating the spinal cord and other surrounding biological tissue outside the focal area between the disc plates to above 44° C.;

monitoring the patient's physical location relative to the transducers, and moving the focal area in response to patient movement, so that the ultrasonic fields from the two laterally spaced obliquely directed therapeutic ultrasonic transducers are accurately focused in the area between the patient's intervertebral disc plates;

providing the controlling signal to the phased array transducers by activating and deactivating selected transducers in order to achieve a target strength of the ultrasonic field as well as a target time period; and controlling the ultrasonic transducers of the treatment transducer such that undesired temperature changes in the intervertebral disc are prevented.

15. The method according to claim 14 further comprising the step of sensing the temperature of a point on/in the patient outside the focal area between the obliquely directed focused ultrasonic fields, and in close proximity to the area of the patient's spinal cord.

16. The method according to claim 15 further comprising the step of supervising the temperature in the intervertebral disc by ultrasound during treatment.

17. The method according to claim 14 wherein:

the ultrasonic field created has a frequency in the range of 0.5 to 2.5 megahertz, the time period for so treating the intervertebral disc area between the plates from the ultrasonic fields is in the range of 5 to 60 minutes, and the step of heating the tissue in the focal area of the ultrasonic fields is to a temperature in the range of 45° C. to 50° C., and the focal area is the nucleus pulposus.

18. The method according to claim 14 wherein the step of focusing the ultrasonic fields in a focal area are facilitated by transducer elements each having a concave spherical transducer surface.

19. The method according to claim 14 further comprising the step of providing a resilient liquid-filled compliant container adjacent to the skin of the patient, and directing the focused ultrasonic fields from the transducers through such liquid, then through the patient's skin, into the focal area between the intervertebral disc plates of the patient.

20. The method according to claim 14 further comprising:

the step of providing a computerized system to automate treatment and to monitor time, intensity, temperature and location of the focal area wherein the system executes commands comprising the steps of setting parameters to establish temperature in the focal area, the time for treatment, and the intensity;

inputting the location of the focal area to be heated;

calculating time delays for various elements in at least two therapeutic transducers so that the focal area is located correctly;

starting and maintaining treatment by transmitting ultrasonic fields from at least two directions to meet at the focal area, the ultrasonic fields having the set intensity and heating the focal area to the set temperature;

looping to check for impermissible movement of the input focal area relative to an actual focal area, and impermissible temperature range in the actual focal area;

selecting to reset treatment or terminate treatment if impermissible movement and/or temperature are detected; and terminating treatment upon completion thereof when the set time expires.

* * * * *